(12) United States Patent
Ikemoto et al.

(10) Patent No.: US 8,273,719 B2
(45) Date of Patent: Sep. 25, 2012

(54) WRINKLE-DIMINISHING AGENT

(75) Inventors: Takeshi Ikemoto, Kanagawa (JP); Aya Komiya, Kanagawa (JP); Akinori Haratake, New York, NY (US)

(73) Assignee: Kao Corporation, Tokyo (JP)

( * ) Notice: Subject to any disclaimer, the term of this patent is extended or adjusted under 35 U.S.C. 154(b) by 431 days.

(21) Appl. No.: 12/465,780

(22) Filed: May 14, 2009

(65) Prior Publication Data
US 2009/0227525 A1 Sep. 10, 2009

Related U.S. Application Data

(62) Division of application No. 10/586,877, filed as application No. PCT/JP2005/000736 on Jan. 21, 2005, now abandoned.

(30) Foreign Application Priority Data

Jan. 21, 2004 (JP) ................................. 2004-012764

(51) Int. Cl.
*A01N 43/04* (2006.01)
*A61K 31/70* (2006.01)
(52) U.S. Cl. ........................................ 514/25; 424/1.73
(58) Field of Classification Search .................... 514/25; 424/1.73
See application file for complete search history.

(56) References Cited

U.S. PATENT DOCUMENTS

| 2003/0054021 A1 | 3/2003 | Dalko et al. |
| 2003/0165547 A1 | 9/2003 | Picard-Lesboueyries et al. |

FOREIGN PATENT DOCUMENTS

| JP | 62-164609 A | 7/1987 |
| JP | 6-227959 A | 8/1994 |
| JP | 7-165567 A | 6/1995 |
| JP | 7-179328 A | 7/1995 |
| JP | 9-040531 A | 2/1997 |
| JP | 9-249549 A | 9/1997 |
| JP | 2000-169358 A | 6/2000 |
| JP | 2001-328940 A | 11/2001 |
| JP | 2002-104921 A | 4/2002 |
| JP | 2002-255781 | * 9/2002 |
| JP | 2003-226655 A | 8/2003 |
| JP | 2004-107250 | * 4/2004 |
| JP | 2004-107250 A | 4/2004 |
| WO | WO 02/094212 A1 | 11/2002 |

OTHER PUBLICATIONS

CAS abstract Accession No. 2004:289524 for JP2004-107250. Yokota, T., Yamazaki, S., Suzuki, K., Ikemoto, T., Hikima, R., Matsumoto, M. (2004) Sensitive skin-improving agents and nerve growth factor generation inhibiting agents for skin compositions.*
Machine translation of JP2004-107250 (2004) [online] [Retrieved Jun. 22, 2011] Retrieved from the internet <http://dossier1.ipdl.inpit.go.jp/AIPN/odse_top_dn.ipdl?N0000=7400>.*
Sato, T., Takeuchi, H., Takahashi, K., Kurosu, J., Yoshida, K., Tsugane, T., Shimura, S., Kino, K., Kirimura, K. (2003) Selective α-Glucosyl Transfer Enzyme of *Xanthomonas campestris* WU-9701. Journal of Bioscience and Bioengineering, vol. 96, No. 2, p. 199-202.*
Abstract JP2002-255781 (2002) [online] [Retrieved Jan. 1, 2012] Retrieved from the internet <http://worldwide.espacenet.com/numberSearch?locale=en_EP>.*
Machine translation of JP2002-255781 (2002) [online] [Retrieved Jun. 22, 2011] Retrieved from the internet <http://dossier1.ipdl.inpit.go.jp/AIPN/odse_top_dn.ipdl?N0000=7400>.*
Hamada et al., "Effect of clove bud oil related eugenyl glucoside on hair growth", Fragrance Journal, vol. 29, No. 3, (2001), pp. 47-52.
Wang et al., "Isolation and Structural Elucidation of Aroma Constituents Bound as Glycosides from Sage (*Salvia officinalis*)", Journal of Agricultural and Food Chemistry, vol. 46 (1998), pp. 2509-2511.
Takeshi Ikemoto, US PTO Office Action, U.S. Appl. No. 10/586,877, Feb. 26, 2009, 13 pgs.
Takeshi Ikemoto, US PTO Office Action, U.S. Appl. No. 10/586,877, Aug. 27, 2008, 9 pgs.

* cited by examiner

*Primary Examiner* — Scarlett Goon
(74) *Attorney, Agent, or Firm* — Foley & Lardner LLP

(57) ABSTRACT

An antiwrinkle agent which is highly effective in alleviating wrinkles caused by the photoaging. The present invention relates to an antiwrinkle agent comprising an eugenyl glycoside.

4 Claims, No Drawings

WRINKLE-DIMINISHING AGENT

CROSS-REFERENCE TO RELATED APPLICATIONS

This application is a Divisional of U.S. application Ser. No. 10/586,877, filed Jul. 21, 2006, which is the National Stage of International Application No. PCT/JP2005/000736, filed Jan. 21, 2005, which is based upon and claims the benefit of priority from prior Japanese Patent Application No. 2004-012764, filed Jan. 21, 2004, the entire contents of all of which are incorporated herein by reference in their entirety.

FIELD OF THE INVENTION

The present invention relates to an antiwrinkle agent comprising an eugenyl glycoside having excellent wrinkle alleviating effect on the wrinkles formed due to aging, especially on exposed skin portions, and being capable of keeping skins healthy from the viewpoint of dermatology and beauty.

BACKGROUND ART

In all living bodies including human being, organs gradually deteriorate after they are born and as they grow old, and the functions of some of them stop later and the number of the organs of which functions have stopped reaches a certain value or more, resulting in a death. A process in which the functions gradually deteriorate is called aging. Skins are affected directly by their environments, and have an important function to maintain the conditions inside a living body and hence all functions of the skins rarely stop, but the skin is an organ likely to remarkably show signs of aging, such as wrinkles or spots, being of dull color, or being loose, which are marked especially at skin portions exposed to daylight.

As the skin ages, protection of the skin against stimulation, such as oxidation stress, weakens to cause the conditions inside the skin to be bad, thus promoting the aging. Particularly, the skin portion exposed to daylight is always exposed to strong oxidation stress such as ultraviolet radiation, and hence the progress of aging is remarkable in the exposed skin. Such a change of the skin is called photoaging, and in the skin which has suffered from photoaging, the epidermis increases in thickness and the dermis reduces in collagen which is a major constituent of the dermis, to cause deep or large wrinkles on the skin surface, leading to beauty problems.

As a substance having a wrinkle alleviating effect on the wrinkles caused by the photoaging, retinoic acid is used as a prescription drug in the United States, but the retinoic acid has a strong side effect and has a problem from the viewpoint of safety, and hence it has not yet been approved in Japan. Further, as substances for alleviating the wrinkles, retinol (vitamin A) which is believed that it is absorbed by a body and then converted to retinoic acid to exhibit the effect, ascorbic acid (vitamin C) having an antioxidant action and a collagen synthesis promotion effect, and tocopherol (vitamin E) having a strong antioxidant action have been proposed (see, for example, Japanese Unexamined Patent Publication Nos. Hei 7-165567 and Sho 62-164609), but these substances disadvantageously do not have a satisfactory effect. Therefore, a satisfactorily effective and safe substance for diminishing the wrinkles has not yet been developed.

Eugenol is known as a fragrance component of clove which is a kind of spice, and it is known that the eugenol is generally used as an analgesic agent for toothache and others, and further has a blood flow promotion effect or demelanizing effect when applied to a surface topical site, and it is applied to a dermis collagen fascicular reconstruction agent (see, for example, Japanese Unexamined Patent Publication Nos. Hei 9-249549, Hei 6-227959, and 2002-104921). However, the eugenol has problems in that it has a characteristic odor and that it induces sensitization when used in a high concentration (see, for example, Contact Dermatitis, 1992, No. 27, p. 98-104).

The present inventors have found that a glycoside formed from eugenol can solve these problems, and have proposed a hair tonic and a sustained-release aromatic composition for human surface skin (see Japanese Unexamined Patent Publication Nos. Hei 9-40531 and Hei 7-179328), but they have made no studies on a wrinkle alleviating effect of the glycoside of eugenol.

DISCLOSURE OF THE INVENTION

Problems to be Solved by the Invention

It is an object of the present invention to provide an antiwrinkle agent comprising an eugenyl glycoside being capable of keeping skins healthy from the viewpoint of beauty and having excellent wrinkle alleviating effect on the wrinkles markedly formed especially on exposed skin portions.

In view of the above, the present inventors have conducted extensive and intensive studies mainly on eugenol derivatives. As a result, it has been found that the antiwrinkle agent comprising an eugenyl glycoside is advantageous not only in that it can keep skins healthy from the viewpoint of beauty, but also in that it has excellent wrinkle alleviating effect on the wrinkles formed due to aging, especially on exposed skin portions, and thus the present invention has been completed.

The present invention is directed to an antiwrinkle agent comprising an eugenyl glycoside. Further, the present invention is directed to the antiwrinkle agent wherein the eugenyl glycoside is eugenyl-β-D-glucoside.

In the present invention, there is provided an antiwrinkle agent which is advantageous not only in that it has excellent wrinkle alleviating effect on the wrinkles formed due to aging, especially on exposed skin portions, but also in that it keeps skins healthy from the viewpoint of dermatology and beauty.

BEST MODE FOR CARRYING OUT THE INVENTION

Hereinbelow, embodiments of the present invention will be described in detail.

Eugenol is generally known as a fragrance component of clove which is a kind of spice. It is known that the eugenol has an analgesic effect, and it is also used as an analgesic agent for toothache and others. The eugenyl glycoside in the present invention can be obtained by forming a glycoside from eugenol with an O-glycoside bond by a general method.

The glycosyl residue of the eugenyl glycoside in the present invention is monosaccharide or oligosaccharide, and examples include monosaccharides such as glucose, galactose, xylose, rhamnose, mannose, glucosamine, and galactosamine; and disaccharides such as lactose, maltose, sucrose, cellobiose and gentiobiose. Preferred are glucose, galactose, xylose, lactose and maltose. A glycoside has isomers having an α-bond or a β-bond. In the present invention, either any isomer or a mixture of the isomers can be used, but preferred is a glycoside having a β-bond. In the present invention, eugenyl-β-D-glucoside, a D-glucose glycoside of eugenol having a β-bond is especially preferably used from the viewpoint of obtaining the effect.

In the present invention, it is preferred that the amount of the eugenyl glycoside formulated is 0.2 to 5.0% by weight (hereinafter, "%" is given by weight unless otherwise specified), based on the total weight of the antiwrinkle agent. When the amount of the eugenyl glycoside is in this range, the effect aimed at by the present invention can be efficiently and sufficiently achieved. The amount is more preferably 0.3 to 5.0%, further preferably 0.5 to 4.5%, especially preferably 1.0 to 4.0%.

The antiwrinkle agent of the present invention can be formulated in cosmetics for skin, external drug preparation or bath salts, and can be used in the form of, for example, lotion, emulsion, cream or pack. In the antiwrinkle agent of the present invention, in addition to the above-described component, a coloring agent, a fragrance, a preservative, a surfactant, a pigment or an antioxidant can be added in such an amount that the effect of the present invention is achieved.

EXAMPLES

The present invention will be described in more detail with reference to the following Examples and Comparative Examples, which should not be construed as limiting the scope of the present invention.

Examples 1 to 3 and Comparative Examples 1 and 2

The wrinkle alleviating effect of the antiwrinkle agent of the present invention when applied to a skin which had suffered from photoaging was examined by the following test method.
1. Sample and Experimental Animal
1-1. Sample Examples 1 to 3

Eugenyl-β-D-glucoside was added to a 50% (v/v) aqueous ethanol solution (base) in the concentrations shown in Table 1 below.

Comparative Examples

In Comparative Example 1, only the base was used, and in Comparative Example 2, eugenol was added in the concentration shown in Table 1.
1-2: Experimental Animal
A group of ten hairless mice which were ten weeks old at the start of the test was used.
2. Evaluation of Wrinkle Alleviating Effect
2-1. Photoaging Conditions and Evaluation Method Photoaging was caused by irradiating the mice with UVA and UVB once a day and five times per week for continuous eight weeks. A UVA dose of 20 J/cm$^2$ was increased to 25 J/cm$^2$ and then 30 J/cm$^2$ every week, and a UVB dose of 20 mJ/cm$^2$ was increased to 30 mJ/cm$^2$ and then 40 mJ/cm$^2$ every week, and the respective maximum doses were used on and after the third week. The wrinkle alleviating effect was evaluated in respect of the wrinkle score, the dermis collagen content and the epidermis thickness.
Wrinkle Score:

The state of wrinkles was rated in accordance with the method of Bissett et. al. (Photochem Photobiol 46:367-378, 1987). Specifically, the wrinkles were macroscopically evaluated with respect to the size and depth and rated in 4 stages: "large and deep wrinkles can be recognized" was rated 3, "some wrinkles can be recognized" was rated 2, "any wrinkles cannot be recognized" was rated 1, and "normal and fine skin is observed" was rated 0.
Dermis Collagen Content:

Whole skin was sampled and homogenized by a POLYTRON Homogenizer (manufactured by KINEMATICA AG), and then the collagen fraction was extracted and subjected to acid hydrolysis followed by quantitative determination of a hydroxyproline content using an amino acid analyzer (manufactured by JASCO Corporation). The hydroxyproline content per square centimeter was used as a relative index of the dermis collagen content.
Epidermis Thickness:

Whole skin was sampled, and a skin section sample was prepared by a general method, and then subjected to hematoxyline eosin stain and a thickness of the epidermis was measured using an image analysis soft (MicroAnalyzer, manufactured by Nihon Poladigital, K.K.).
2-2. Operation 0.1 mL of an evaluation sample was applied to the hairless mice at their dorsal skins (diameter: about 2.5 cm) once a day and five times per week from the fifth week after the start of the UV irradiation to the fourth week after the termination of the irradiation. After the final application, wrinkle scores were obtained. After killing the mice, a skin was sampled to measure the collagen content (hydroxyproline content per square centimeter) and the epidermis thickness. The wrinkle alleviating effect was evaluated by comparing the wrinkle score, the collagen content, and the epidermis thickness with those in Comparative Example 1 in which only the base was applied.

TABLE 1

| Group | Wrinkle score*) |
|---|---|
| Example 1 (0.2% by weight of eugenyl-β-D-glucoside) applied | 2.4 ± 0.1 |
| Example 2 (2.0% by weight of eugenyl-β-D-glucoside) applied | 2.2 ± 0.2 |
| Example 3 (4.0% by weight of eugenyl-β-D-glucoside) applied | 2.1 ± 0.1 |
| Comparative Example 1 (base only) applied | 2.6 ± 0.1 |
| Comparative Example 2 (2.0% by weight of eugenol) applied | 2.7 ± 0.1 |

*)Value is average ± standard error.

The wrinkle scores are shown in Table 1. The wrinkle scores of the antiwrinkle agent applied groups in Examples 1 to 3 are significantly low as compared to that in Comparative Example 1, which indicates that the antiwrinkle agent comprising the eugenyl glycoside is effective against the wrinkles caused due to the photoaging. Further, the antiwrinkle agent comprising eugenol in Comparative Example 2 did not show the antiwrinkle effect in the wrinkle score.

TABLE 2

| Group | Collagen content*) (μmol/cm$^2$) | Epidermis thickness*) (μm) |
|---|---|---|
| Example 1 applied | 8.8 ± 0.4 | 42.5 ± 2.3 |
| Example 2 applied | 9.2 ± 0.4 | 41.2 ± 4.4 |
| Example 3 applied | 9.3 ± 0.6 | 38.6 ± 1.6 |
| Comparative Example 1 applied | 8.1 ± 0.2 | 57.5 ± 6.8 |
| Comparative Example 2 applied | 7.8 ± 0.5 | 61.1 ± 2.6 |

*)Value is average ± standard error.

The results of the measurements of the collagen content (hydroxyproline content) and the epidermis thickness are shown in Table 2. The collagen content of the antiwrinkle agent applied groups in Examples 1 to 3 was that significantly high as compared to in Comparative Example 1, which indicates that the eugenyl glycoside is effective against the reduction of the dermis collagen content due to the photoaging. Further, the antiwrinkle agent comprising eugenol in Comparative Example 2 did not show the effect on the reduction of the dermis collagen content due to the photoaging.

The epidermis thickness of the antiwrinkle agent applied groups in Examples 1 to 3 was significantly thin as compared to that in Comparative Example 1, which indicates that the eugenyl glycoside is effective in inhibiting the increase of epidermis thickness due to the photoaging. In contrast, the antiwrinkle agent comprising eugenol in Comparative Example 2 did not show the effect of inhibiting the increase of epidermis thickness due to the photoaging. When retinoic acid, of which the wrinkle alleviating effect has been confirmed, was applied to the present evaluation system, it was found that retinoic acid was effective with respect to the wrinkle score and collagen content, but retinoic acid increased the epidermis thickness. This action of retinoic acid to increase the epidermis thickness is one of problems for safety. The eugenyl glycoside had no such an action, and had no problems in a general safety test.

From the results of the present tests, it is apparent that the eugenyl glycoside applied groups in Examples 1 to 3 have a remarkable wrinkle alleviating effect on the wrinkles caused by the photoaging as compared to the group in Comparative Example 1. Further, it has been found that eugenol itself does not have a wrinkle alleviating effect on the wrinkles caused by the photoaging, but a glycoside formed from the eugenol exhibits the effect.

Example 4 and Comparative Example 3

Skin Lotion

Skin lotions having the compositions shown below were individually prepared by the method described below, and the lotions prepared as samples were evaluated with respect to the wrinkle alleviating effect in accordance with the following procedure. Five healthy persons (women; age: 44 to 55) having wrinkles at the corners of their eyes were selected as subjects, and they individually applied about 0.2 ml of each of the skin lotions in Example 4 and Comparative Example 3 to the respective portions of wrinkles at the corners of the left eye and the right eye (about 4 cm$^2$ or 2 cm×2 cm around the corner of the eye per sample) after washing the face in the morning and after bathing in the evening, i.e., twice a day for continuous two months (sixty days). After the final application, they filled in a questionnaire about the conditions of the skins (wrinkles) at the corners of their left and right eyes.

1. Composition of Skin Lotion:

| Ingredients | Amount (%) | |
|---|---|---|
| Ingredient A | | |
| (1) Olive oil | 10.0 | |
| (2) Isopropyl myristate | 1.0 | |
| (3) Polyoxyethylene (20) sorbitan monolaurate | 0.5 | |
| (4) Propylene glycol | 1.0 | |
| (5) Glycerol | 2.0 | |
| Ingredient B | | |
| (6) Methylparaben | 0.1 | |
| (7) Ethanol | 7.0 | |
| (8) Purified water | Balance | |
| Ingredient C | | |
| (9) Eugenyl-β-D-glucoside | 2.0 or 0 | (Example 4) (Comparative Example 3) |

2. Preparation Method

Eugenyl-β-D-glucoside as ingredient C was added to ingredient B and uniformly dissolved, and then ingredient A was added and the resultant mixture was dispersed by stirring and then filled in a container. The contents of the container were uniformly dispersed by shaking before being used.

3. Evaluation

Based on the feedback of the questionnaire, the numbers of the persons who answered that the skin lotion in Example 4 was more effective than that in Comparative Example 3 in individual items for the conditions of the skins (wrinkles) are shown below.

| Item | Number of persons |
|---|---|
| Wrinkles alleviated. | 5 |
| Skin softened. | 4 |
| Skin tensed. | 5 |
| Skin lustered. | 3 |
| Skin brightened. | 4 |

From the results of the present test, it is apparent that the skin lotion in Example 4 considerably alleviated the wrinkles, as compared to that in Comparative Example 3, and further it improved the softness or color tone of the skin which deteriorated due to the photoaging. In addition, the skin lotion in the present invention caused no skin troubles, e.g., no stimulation or no itching.

Example 5

Skin Cream

A skin cream containing eugenyl-β-D-glucoside and having the composition shown below was prepared by the method described below, and twenty healthy persons (women; age: 50 to 55), who preliminarily answered that they had skin troubles of wrinkles at the corners of their eyes, used the skin cream for one week or longer and then filled in a questionnaire.

1. Composition of Skin Cream

| Ingredients | Amount (%) |
|---|---|
| Ingredient A | |
| (1) Bees wax | 2.0 |
| (2) Stearic acid | 5.0 |
| (3) Stearyl alcohol | 5.0 |
| (4) Reduced lanolin | 2.0 |
| (5) Squalene | 20.0 |

| Ingredients | Amount (%) |
|---|---|
| (6) Sorbitan monostearate | 3.0 |
| (7) Polyoxyethylene (20) sorbitan monostearate | 3.0 |
| (8) Propylene glycol | 5.0 |
| Ingredient B | |
| (9) Methylparaben | 0.2 |
| (10) Purified water | Balance |
| Ingredient C | |
| (11) Eugenyl-β-D-glucoside | 2.0 |

2. Preparation Method

Eugenyl-β-D-glucoside as ingredient C was added to ingredient B, and then ingredients A and B were individually dissolved by heating to 80° C. and mixed, and cooled to 30° C. while stirring to prepare a skin cream.

3. Evaluation

After the subjects individually used the skin cream in Example 5 for one week or longer, they filled in a questionnaire about the state of wrinkles in the items shown below. The numbers of the persons who answered that the description in each item was true after using the skin cream are shown below.

| Item | Number of persons |
|---|---|
| Wrinkles alleviated. | 19 |
| Wrinkles reduced in size. | 17 |
| Wrinkles reduced in number. | 5 |
| Wrinkles increased. | 0 |

From the results of the present evaluation, it is apparent that almost all the subjects sensed that their wrinkles alleviated as compared to them before use in Example 5, and the fact that the skin cream was more effective in reducing the size of wrinkles rather than in reducing the number of wrinkles indicates that the skin cream alleviated the wrinkles caused by the photoaging. In addition, the skin cream in the present invention caused no skin troubles, e.g., no stimulation or no itching.

Industrial Applicability

The antiwrinkle agent of the present invention can be formulated in cosmetics for skin, external drug preparation or bath salts, and can be used in the form of, for example, lotion, emulsion, cream or pack, and it is very useful from the viewpoint of skin beauty.

The invention claimed is:

1. A method for reducing wrinkles occurring in photoaging on skin, comprising applying to photoaged skin a composition comprising eugenyl-β-D-glucoside in an amount of 0.2 to 5% by weight based on the weight of the composition.

2. The method according to claim 1, wherein the composition comprises the eugenyl-β-D-glucoside in an amount of 0.3 to 5% by weight based on the weight of the composition.

3. The method according to claim 1, wherein the composition comprises the eugenyl-β-D-glucoside in an amount of 0.5 to 4.5% by weight based on the weight of the composition.

4. The method according to claim 1, wherein the composition comprises the eugenyl-β-D-glucoside in an amount of 1 to 4% by weight based on the weight of the composition.

* * * * *